United States Patent [19]

Rasmussen et al.

[11] 4,265,900

[45] May 5, 1981

[54] N-ARYL-N'-IMIDAZOL-2-YLUREAS

[75] Inventors: C. Royce Rasmussen, Ambler; Henry I. Jacoby, Rydal, both of Pa.

[73] Assignee: McNeilab, Inc., Fort Washington, Pa.

[21] Appl. No.: 88,880

[22] Filed: Oct. 29, 1979

[51] Int. Cl.³ .................. A61K 31/415; C07D 233/88
[52] U.S. Cl. .................................. 424/273 R; 548/315
[58] Field of Search ..................... 548/315; 424/273 R

[56] References Cited

U.S. PATENT DOCUMENTS 3,983,135  9/1976  Rasmussen ........................... 544/321

OTHER PUBLICATIONS

Paget et al., J. Med. Chem. 1969, vol. 12/5, pp. 1010–1015.

*Primary Examiner*—Alan L. Rotman
*Assistant Examiner*—Natalia Harkaway
*Attorney, Agent, or Firm*—Geoffrey G. Dellenbaugh

[57] ABSTRACT

N-aryl-N'-imidazol-2-ylureas useful for their antihypertensive, antidiarrheal, anti-irritable bowel syndrome, and anti-secretory activities.

11 Claims, No Drawings

N-ARYL-N'-IMIDAZOL-2-YLUREAS

FIELD OF THE INVENTION

This invention relates to N-aryl-N-'-imidazol-2-ylureas useful for their antihypertensive, antidiarrheal, anti-irritable bowel syndrome, and anti-secretory activities. Also included within the invention are pharmaceutical compositions comprising these compounds and methods for treatment using these compounds.

BACKGROUND AND PRIOR ART

C. J. Paget, et al., J. Med. Chem., 12, 1010 (1969) report the preparation of benzimidazolureas and their testing for immunosuppressive activity and antiviral activity. For comparative purposes, certain other urea analogs were prepared and tested, including N-imidazol-2-yl-N'-phenylurea, which was considered inactive for the purposes tested. N-(5-Methyl-4-imidazol-4-yl)-N'-phenylurea has been reported by R. Weidenhagen, et al., Ber. 68B, 2205-9 (1935); Chem. Abstr. 30, 2192[10] (1936). This latter compound is a related positional isomer of the unsubstituted phenyl analog of the subject compounds, for which no pharmacological property is disclosed. None of the references disclose or suggest the N-aryl-N'-imidazol-2-ylureas posses any anti-hypertensive, antidiarrheal, anti-irritable bowel syndrome, or anti-secretory activity.

DESCRIPTION OF THE INVENTION

The present invention comprises a novel class of imidazolyl urea compounds of formula

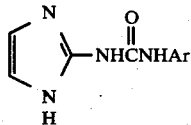

(I)

wherein in the foregoing and subsequent formulas Ar is phenyl substituted with from 1 to 2 substituents each selected from halo, loweralkyl, loweralkoxy, and trifluoromethyl. These compounds differ structurally from the prior art N-imidazol-2-yl-N'-phenylurea in that Ar is substituted phenyl, while in the prior art compound Ar is unsubstituted phenyl. Certain of the subject compounds also differ from the prior art in that they are useful antihypertensive agents which do not simultaneously increase heart rate, while the prior art compound significantly increases heart rate. The subject compounds also possess significantly more potent gastrointestinal activity than that possessed by the prior art compound.

The expressions "loweralkyl" and "loweralkoxy" are intended to embrace straight chain or branched alkyl and alkoxy substituents, respectively, which have from 1 to 3 carbon atoms, such as, for example, methyl, ethyl, n-propyl, isopropyl, and the like loweralkyls, and, respectively, methoxy, ethoxy, n-propoxy, isopropoxy, and the like loweralkoxys. The preferred loweralkyl is methyl and the preferred loweralkoxy is methoxy. The expression "halo" includes chloro, bromo, and fluoro, with chloro and bromo being preferred.

The foregoing urea compounds occasionally form solvates with alcoholic solvents such as, for example, methanol and t-butanol. Such solvates are included within the scope of the subject invention.

The subject compounds of formula (I) form salts with pharmaceutically-acceptable strong acids such as, for example, hydrochloric, hydrobromic, sulfuric, methosulfuric, phosphoric, ethanesulfonic, benzenesulfonic, p-toluene sulfonic, β-naphthalenesulfonic, ethane-1,2-disulfonic, dodecyl hydrogen sulfate, nitric, methane sulfonic, and the like acids. These therapeutically active pharmaceutically-acceptable strong acid addition salts are also part of the present invention. These salts may be converted back to free base form by treatment with a base (e.g., sodium hydroxide, sodium carbonate, potassium bicarbonate, triethylamine, etc.).

PREPARATIVE ROUTES

The urea compounds of formula (I) may be prepared by the reaction of 2-aminoimidazole of formula (II) with an appropriate aryl isocyanate of formula (III) as shown in the following reaction scheme:

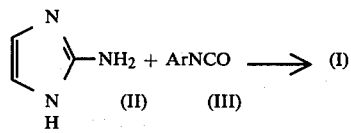

Since the 2-aminoimidazole is generally prepared and stored as the hydrogen halide (preferably chloride) addition salt, the first step is the reaction of the addition salt with a basic reagent to form the free base.

The neutralization reaction may be carried out by employing bases such as triethylamine or, alternatively, lithium hydride in a solvent such as dimethylformamide (DMF), dimethylsulfoxide (DMSO), and the like in which the corresponding free base is soluble.

When the neutralization reaction is carried out employing a base such as triethylamine, the base may be added to a solution of 2-aminoimidazole hydrochloride, and the resulting mixture may be stirred at ambient temperature for short periods up to about one hour. Upon addition of triethylamine an immediate precipitate of triethylamine hydrochloride forms, which may be filtered off, if desired, and the filtrate used for reaction with the aryl isocyanate. Alternatively, the unfiltered mixture may also be employed directly for the reaction with the aryl isocyanate.

When the neutralization reaction is carried out with lithium hydride as the base, the preferred method is the portion-wise addition of a solution of 2-aminoimidazole hydrohalide to a stirred suspension of lithium hydride in a solvent such as dimethylformamide. When the addition is complete, the reaction mixture is stirred for an additional period until cessation of hydrogen evolution. The resulting solution of the free base may then be employed in the reaction with the aryl isocyanate.

The reaction between the 2-aminoimidazole of formula (II), prepared by one of the methods above described, and the aryl isocyanate of formula (III) may be carried out by the dropwise addition of the aryl isocyanate to a solution of the 2-aminoimidazole in an inert solvent such as, for example, DMF, DMSO, 1-methyl-2-pyrrolidinone, tetrahydrofuran (THF), dioxane, 1,2-dimethoxyethane, tetramethylenesulfoxide, tetramethylenesulfone, and the like. The aryl isocyanate may be added neat or in solution in an inert solvent. Substantially equimolar amounts of the reactants are employed. The reaction is preferably carried out at ambient temperature for from about one hour to several hours. As the result of these operations the desired N-aryl-N'-imidazol-2-ylurea product is formed in the reaction mixture and may be recovered by conventional procedures, either as the free base or as the strong acid addition salt, as discussed above.

Certain of the compounds, upon recrystallization from alcohols or solvent mixtures containing alcohols, are found to form crystalline solvates with these alcohols.

The starting materials of formulas (II) and (III) are wellknown or may be prepared by known methods.

BIOLOGICAL ACTIVITY

The compounds of the invention are useful for their antihypertensive and gastrointestinal activity as demonstrated in the tests described below. The term "gastrointestinal activity" designates activity on at least one of the antidiarrheal, anti-irritable bowel syndrome, and anti-secretory activity tests given below. The preferred compounds having gastrointestinal activity exhibit activity in at least two and generally in all three of these tests for gastrointestinal activity given below.

A. ANTIHYPERTENSIVE ACTIVITY

Certain of the subject imidazolylurea compounds have been found to alleviate hypertension and further, to generally accomplish this without an accompanying increase in heart rate. Agents which have an antihypertensive effect without increasing but either maintaining or decreasing heart rate, are considered most useful for beneficially treating a hypertensive subject. The extent to which a compound possesses these properties may be determined in the following antihypertensive test on rodents.

RODENT ANTIHYPERTENSIVE SCREEN.

This test evaluates compounds for effects on arterial pressure and heart rate. In this test, systolic, diastolic, and mean arterial [⅓ (systolic-diastolic)+diastolic] blood pressures and heart rate of spontaneously hypertensive rats are monitored directly via an aortic cannula. Rats are anesthetized with an inhalation anesthetic (methoxyflurane or ether). The left carotid artery is isolated and cannulated. The tip of the cannula is advanced to the aorta and the cannula is exteriorized behind the neck at the level of the scapula. Animals are placed in individual cases and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of two hours. Each animal serves as his own control.

Maximal antihypertensive activity is scored in the following manner:

| Decrease in pressure (mm of Hg) | Activity Score |
| --- | --- |
| ≦15 | none |
| 16–30 | weak |
| 31–45 | moderate |
| ≧46 | marked |

The onset of antihypertensive activity represents the time (hrs) at which blood pressure is decreased by more the 15 mmHg. The duration (hrs) of antihypertensive activity is the difference between the time of onset and the time that blood pressure returns to within 15 mmHg of the control value. The maximal change in heart rate is determined and recorded as beats per minute. Generally, changes in heart rate of greater than 20 beats per minute are considered significant.

The results of this test employing three or four rats for each compound and administering the compounds p.o. at a dose of 35 mg/kg body weight are given in Table I below. These results show that certain of the subject compounds possess beneficial antihypertensive activity, while certain perferred compounds also possess the desirable property of simultaneously maintaining or lowering normal heart rate.

Preferred compounds of the subject invention for anti-hypertensive activity are those of formula (I) wherein Ar is 2,6-disubstituted phenyl. These preferred compounds are particularly effective antihypertensive agents, while generally maintaining or lowering the normal heart rate. It should be noted in this regard that the administration of many antihypertensive agents is accompanied by a compensatory reflexly-mediated increase in heart rate. It is a surprising and extremely useful property of these preferred compounds that they actually lower the heart rate, as compared to the prior, art compound which significantly increases the heart rate. These preferred compounds also generally exhibit considerably longer duration of antihypertensive action (on the order of from six to 36 hours) when compared to the prior art compound in which Ar is unsubstituted phenyl (two to four hours).

More preferred compounds for antihypertensive activity are those of formula (I) wherein Ar is 2,6-disubstituted phenyl and the substituents are each selected from the group consisting of chloro, bromo, methyl and ethyl, provided that not more than one is ethyl.

B. GASTROINTESTINAL ACTIVITY

The subject imidazolyl urea compounds have been found to possess gastrointestinal activity, as demonstrated by activity in at least one of the following tests.

Diarrhea is a distressing and debilitating condition which is widespread among the world's population. In certain diseases, this enteric disorder can be the cause of a high degree of morbidity and even of mortality. Compounds which alleviate the symptoms of diarrhea are thus of significant benefit to medical science. The antidiarrheal activity of the subject compounds was determined by the following Castor Oil test.

Peptic ulcer is a widespread debilitating condition. It is well-known that excessive secretion of gastric hydrochloric acid can lead to ulceration of the mucous membrane of the gastrointestinal tract. The use of gastric anti-secretory agents is thus desirable as an aid in the prevention and amelioration of distress in peptic ulcer disease. The anti-secretory activity of the subject compounds was determined by the following Acute Gastric Fistula Rat Test.

Irritable bowel syndrome is a functional disorder characterized primarily by abdominal pain, but also by diarrhea and constipation and like symptoms. It is believed that the pain associated with this syndrome is due to excessive sensitivity to distention of the bowel caused either by intestinal gas and/or fecal material. Treatments which would provide relief from the discomforts associated with such symptoms and/or the disorder which produce such symptoms are highly desirable.

The anti-irritable bowel syndrome activity of the subject compounds was determined by the following Glass Bead test.

CASTOR OIL TEST.

Female Sprague-Dawley rats (140–160 g) are used for this study. Twenty-four hours before testing, the rats are individually caged and fasted; water given ad libitum during fast.

The test compounds are given orally suspended in 0.5% methocel using a volume of 1 ml/100 g body weight. Five rats are used for each compound dose tested. Control rats receive the test vehicle. One hour later, each rat receives a single dose of castor oil (1 ml/rat orally) and is returned to his cage and is given access to food and water for the remainder of the experiment.

Rats fasted twenty-four hours will have diarrhea usually within one hour after castor oil administration. The animals are observed for diarrhea every hour for three to five hours. A positive or negative response is used. The results are given as the $ED_{50}$ dose, which is that dose which protected 50% of the treated rats from diarrhea.

ACUTE GASTRIC FISTULA RAT TEST.

Female Sprague-Dawley rats are used for this study. The weights range from 125–150 g; however, weights in any given test have a range of ±20 g. The rats are fasted twenty-four hours before testing, water is given ad libitum. At the time of fasting, the rats are placed in individual cages with wide mesh bottoms. This eliminates the problem of cannibalism and coprophagia.

On the day of testing, the rats are weighed beforehand to determine the weight range and to allow for even distribution.

Surgery is carried out under light ether anesthesia. A mid-line incision is made on the abdomen about 1½ cm long and the stomach is exposed. If, at this point, the stomach is filled with food or fecal material, the rat is discarded.

Using 4-0 Mersiline suture, a purse string stitch is placed on the fundic portion of the stomach taking care to avoid any blood vessels in the area. A small nick is made into the stomach in the center of the purse string and a cannula, consisting of a small vinyl tube with a flange on one end, is put into the stomach and the purse string is closed tightly around the flange. Immediately following this, the test compound (usually about 20 mg/kg) is administered intraduodenally using a volume of 0.5 ml per 100 g body weight. The abdominal wall and skin are closed simultaneously with three to four 18 mm wound clips. The rat is then placed in a box containing a longitudinal slit which allows the cannula to hang freely and the rat is able to move about unencumbered.

At the completion of the procedure, the time is marked zero minutes. The rat is allowed to stabilize for 30 minutes, at which time the collection tube is discarded and replaced with a clean collection tube to receive the gastric juice. Only a one hour collection is made for a screening study. In evaluation studies, one and two hour collections are made. At the end of the study, the cannula is pulled out and the rat is sacrificed.

The gastric contents collected are drained into a centrifuge tube and centrifuged to pack down the sediment. The volume is read and a one ml aliquot of the supernatant is put into a beaker containing distilled water and titrated to pH 7 using 0.01 N NaOH.

Mean values are determined for volume, titratable acid and total acid output where volume equals total ml of gastric juice minus sediment, titratable acid (mEq/l equals the amount of 0.01 N NaOh needed to titrate the acid to pH 7 times 10 and total acid output equals titratable acid times volume. Results are reported in percent inhibition over control values.

GLASS BEAD TEST.

The extent to which a compound is effective in providing relief for irritable bowel syndrome may be determined by a test in which a glass bead is inserted into the rectum and the lapse of time between insertion and expulsion of the bead determined. Compounds which are effective in decreasing the sensitivity to distension of the colonic wall delay the expulsion of the bead.

The test is carried out with male albino mice of 18–25 g body weight using groups of five mice for each compound dose tested. The initial screen dose selected for all compounds is 50 milligrams per kilogram of body weight (mg/kg) administered orally in a volume of 0.1 milliliter per 10 grams of body weight. The control groups receive the vehicle, 0.5 percent methocel, used for both oral and intraperitioneal administration. The mice are fasted one hour before testing and the test drugs are given one hour prior to glass bead insertion.

At the end of the pretreatment time, the mouse is picked up and held firmly in one hand with his abdomen facing the technician. The glass bead of 3 millimeters in diameter is positioned at the rectum and using a pinching action with a thumb and forefinger, the bead is pushed into the rectum. Then using a glass rod of 3 millimeters in diameter which has been lubricated with 0.5 percent methocel to facilitate insertion, the glass bead is pushed up into the rectum a distance of 2 centimeters using a slow gentle turning motion. The mice are timed as a group using the last mouse inserted as zero time and the number of beads expelled in a group at different timed intervals are recorded. The groups are based on timed intervals of 0 to 5 minutes, 5 to 10 minutes, 10 to 20 minutes, 20 to 40 minutes and greater than 40 minutes. They are given the activity index values of 0, 1, 2, 3, and 4, respectively. Mice who have not expelled their beads by the 40-minute cutoff time are examined for perforations. Those mice whose colons are perforated are eliminated from the group. The sum of the values divided by the number of mice or beads is termed the activity index for the drug tested. The $ED_{50}$ is determined by regression lines using the method of least squares. The $ED_{50}$ is arbitrarily assigned as that dose causing an activity index of 2.

The results of these three tests are given in Table I below, which results show the gastrointestinal activity of the subject compounds.

A group of preferred compounds, particularly useful for their gastrointestinal activities, are those of formula (I) wherein Ar is selected from the group consisting of 2,6-disubstituted phenyl, 2-substituted phenyl, 3-substituted phenyl wherein the substituent is other than halo, and 3,4-disubstituted phenyl. Especially preferred gastrointestinally active compounds of the invention are those of formula (I) wherein Ar is 2,6-disubstituted phenyl.

Preferred compounds for anti-secretory activity are those of formula (I) wherein Ar is other than 3-chlorophenyl. Preferred compounds for anti-irritable bowel syndrome activity are those of formula (I) wherein Ar is 2,6-dihalophenyl; 2-halo-6-loweralkylphenyl; or 2,6-dimethylphenyl; provided that halo includes chloro and bromo and loweralkyl includes methyl and ethyl. Preferred compounds for antidiarrheal activity are those of formula (I) wherein Ar is 2,6-disubstituted phenyl, wherein said substituents are selected from the group consisting of chloro, bromo, and methyl.

In view of the antihypertensive activity of certain of the subject compounds of formula (I), there is provided herein a method of treating hypertension or alleviating high blood pressure in a subject (man or animal) in need of said treatment which comprises systemically administering to said subject a therapeutically effective antihypertensive or arterial blood pressure reducing amount of one of said compounds, preferably in admixture with a pharmaceutically-acceptable carrier. Operable dosage ranges for treatment of hypertension are from about 0.05 to about 100 mg/kg of body weight.

In view of the anti-secretory activity of certain of the subject compounds of formula (I), there is provided herein a method of inhibiting gastric acid secretion in a gastric hyperacid subject (man or animal) which comprises systemically administering to said subject a therapeutically effective gastric acid secretion inhibiting amount of one of said compounds, preferably in admixture with a pharmaceutically-acceptable carrier. Operable dosage ranges for anti-secretory effect are from about 0.05 to about 50 mg/kg of body weight.

In view of the antidiarrheal activity of certain of the subject compounds of formula (I), there is provided herein a method for treatment of diarrhea in a subject (man or animal) in need of such treatment which comprises systemically administering to said subject a therapeutically effective antidiarrheal amount of one of the compounds, preferably in admixture with a pharmaceutically-acceptable carrier. Operable dosage ranges are from 0.05 to about 100 mg/kg of body weight.

Finally, in view of the activity of certain of the subject compounds of formula (I) to treat irritable bowel syndrome, there is provided a method of treatment to alleviate the symptoms of this syndrome is a subject (man or animal) in need of said treatment which comprises systemically administering to said subject an amount of one of said compounds therapeutically effective to alleviate the symptoms of irritable bowel syndrome, preferably in admixture with a pharmaceutically-acceptable carrier. Operable dosage ranges are from about 0.05 to about 100 mg/kg of body weight.

A further aspect of the present invention is pharmaceutical compositions useful for at least one of the abovedisclosed activities in which a compound of formula (I) is combined as the active ingredient in intimate admixture with a pharmaceutically-acceptable carrier according to conventional pharmaceutical compounding techniques. This carrier may take a wide variety of forms depending upon the form of preparation desired for administration, e.g., oral or parenteral.

In preparing the compositions in oral dosage form, any of the usual pharmaceutical media may be employed, such as, for example, water, glycols, oils, alcohols, flavoring agents, preservatives, coloring agents and the like (in the case of oral liquid preparations such as, for example, suspensions, elixirs, and solutions) or carriers such as starches, sugars, diluents, granulating agents, lubricants, binders, disintegrating agents, and the like (in the case of oral solid preparations such as, for example, powders, capsules, and tablets). Because of their ease of administration, tablets and capsules represent the most advantageous oral dosage unit form, in which case solid pharmaceutical carriers are obviously employed. If desired, tablets may be sugar-coated or enteric-coated by standard techniques.

For parenterally administered compositions, the carrier will usually comprise sterile water, although other ingredients, for example to aid solubility or for preservative purposes, may be included. Injectable suspensions may also be prepared, in which case appropriate liquid carriers, suspending agents, and the like may be employed.

The pharmaceutical compositions herein will generally contain, per dosage unit (e.g., tablet, capsule, powder injection, teaspoonful, and the like), from about 1 mg to about 500 mg of the active ingredient.

The therapeutic activity of exemplary compounds of the invention (and for comparison the prior art compound) are given on the following Table I, wherein ΔMAP is the change in mean arterial blood pressure in mm of Hg, ΔHR is the mean change in heart rate in beats/minute and duration is the number of hours of activity, all on administration of 35 mg/kg body weight of test compound. The anti-secretory activity is given as percent inhibition on administration of 20 mg/kg body weight of the test compound. The glass bead (anti-irritable bowel) activity and the antidiarrheal activity are given as the $ED_{50}$ value in mg/kg body weight. These test results are provided to illustrate the invention but not to limit the scope thereof.

TABLE I

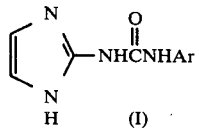

(I)

| | | Antihypertensive | | | Gastrointestinal | | | |
| | Ar | ΔMAP | ΔHR | duration | anti-secretory activity | glass bead activity | antidiarrheal activity | CPD# |
|---|---|---|---|---|---|---|---|---|
| (1)* | phenyl | −34 | +60 | 2–4 | 6% | 138 | NT | x-876 |
| (2) | 2,6-dimethylphenyl | −49 | −92 | 6–12 | 59% | 11.5 | 3.4 | 4159 |
| (3) | 3-chlorophenyl | −30 | +32± | 16–18 | 6% (0% @40 mg/kg) | NA @50 | NT | 4160 |
| (4) | 2,6-dichlorophenyl | −54 | −48 | 30 | 59% | 6.9 | 0.6 | 4217 |
| (5) | 2,6-diethylphenyl | −17 (−40)+ | +36 (−78)+ | 82% (2)+ | 183 | NT | 4225 | |
| (6) | 2-trifluoromethylphenyl | NA | | | 38% | NA @50 | NT | 4227 |
| (7) | 3-methoxyphenyl | NA | | | 49% | 92 | NT | 4228 |

TABLE I-continued $$\text{Structure (I): imidazole-NHCNHAr with C=O}$$

| | Ar | Antihypertensive ΔMAP | ΔHR | duration | Gastrointestinal anti-secretory activity | glass bead activity | antidiarrheal activity | CPD# |
|---|---|---|---|---|---|---|---|---|
| (8) | 2-methylphenyl | NA | | | 47% | 116 | NT | 4231 |
| (9) | 3-trifluoromethylphenyl | −17 | +32± | — | 61% | 192 | NT | 4232 |
| (10) | 3-methylphenyl | NT | | | 67% | 134 | NT | 4238 |
| (11) | 2-ethyl-6-methylphenyl | −31 | −60 | 6–12 | 60% | 110 | ca. 30 (Mouse) | 4246 |
| (12) | 2-chlorophenyl | NA | | | 34% | NA @200 | NT | 4247 |
| (13) | 2-chloro-6-methylphenyl | −36 | −72 | 12–18 | 47% | 6 | >1.6 | 4257 |
| (14) | 2,6-dibromophenyl | −38 | −60 | 3 | 0% (96% @25 mg/kg p.o.) | 2.6 | 17 | 4319 |
| (15) | 2,6-diisopropylphenyl | −17 | −84 | — | 63% | NA @100 | NT | 4320 |
| (16) | 3,4-dimethylphenyl | −34 | −28 | 2 | 52% | NA @200 | NT | 4326 |
| (17) | 4-chlorophenyl | NT | | | (28% @13.9 mg/kg) | NT | NT | 4382 |
| (18) | 4-methylphenyl | NT | | | (18% @40 mg/kg) | NT | NT | 4383 |
| (19) | 2-methoxyphenyl | −20 | −24 | 1 | 39% | NA @50 | NT | 4422 |
| (20) | 4-methoxyphenyl | NT | | | (39% @23.8 mg/kg) | NT | NT | 4423 |
| (21) | 2-isopropylphenyl | NT | | | 39% | NA @50 | NT | 4481 |
| (22) | 2,4-dimethylphenyl | NA | | | 64% | NA @100 | NT | 4483 |
| (23) | 2,5-dimethylphenyl | NA | | | 38% | NA @100 | NT | 4484 |
| (24) | 2,6-dimethoxyphenyl | −17 | −67 | 0.5 | NT | NA @50 | NT | 4834 |
| (25) | 2,6-difluorophenyl | −22 | +32 | 24 | NT | NA @50 | NT | 4836 |

*Prior Art Compound
+ at dose of 30 mg/kg i.p.
± not significant due to wide variability of heart rate among test animals
NA - not active at dose tested
NT - not tested .

EXAMPLE I

N-(2,6-Dimethylphenyl)-N'-(1H-Imidazol-2-yl)urea-4159

To a solution of 12.08 g (0.101 mole) of 2-aminoimidazole hydrochloride in 25 ml of dimethylformamide was added 10.3 g (0.103 mole) of dry triethylmaine to produce 2-aminoimidazole and triethylamine hydrochloride. To the resulting solution was then added with stirring in one portion 14.72 g (0.1 mole) of 2,6-dimethylphenyl isocyanate, whereupon a reaction took place with evolution of heat and separation of product in the mixture. About 75 ml of dimethylformamide was then added and the stirring continued for about one-half hour. At the end of this period, water was added to precipitate the product and the latter recovered by filtration, washed and recrystallized from acetone/water to obtain pure crystalline N-(2,6-dimethylphenyl)-N'-(1H-imidazol-2-yl)-urea, m.p. (225) 230°–275° C. (dec).

Anal: Calcd for $C_{12}H_{14}N_4O$: C, 62.59; H, 6.13; N, 24.33; Found: C, 62.45; H, 6.15; N, 24.38.

EXAMPLE II

N-(2,6-Dimethylphenyl)-N'-(1H-imidazole-2-yl)urea. Hemimethanolate-4159-99

To a stirred suspension of 0.350 g (0.044 mole) of lithium hydride in 10 ml of dimethylformamide under nitrogen atmosphere was added dropwise a solution of 5.26 g (0.044 mole) of 2-aminoimidazole hydrochloride in 50 ml of dimethylformamide. Stirring was continued for about 2.5 hours at room temperature to complete the formation of 2-aminoimidazole, signaled by the cessation of hydrogen evolution. To the resulting mixture was added dropwise with stirring 6.48 g (0.044 mole) of 2,6-dimethylphenyl isocyanate. Stirring was continued for a further 3.5 hours at room temperature to complete the formation of the N-(2,6-dimethylphenyl)-N'-(1H-imidazol-2-yl)urea product. Water was added to precipitate the product, which was then recovered and recrystallized twice from methanol to obtain a white solid sintering about 260° C. NMR analysis showed it to be a hemimethanolate of N-(2,6-dimethylphenyl)-N'-(1H-imidazol-2-yl)urea.

Anal: Calcd for $C_{12}H_{14}N_4O \cdot \frac{1}{2}CH_3OH$: C, 60.96; H, 6.55; N, 22.75; Found: C, 60.63; H, 6.63; N, 22.51.

EXAMPLE III

N-(3-Chlorophenyl)-N'-(1H-imidazol-2-yl)urea-4160

To a solution of 5.26 g (0.044 mole) of 2-aminoimidazole hydrochloride in 50 ml of dimethylformamide was added with stirring to a suspension of 0.350 g (0.044 mole) of lithium hydride in 10 ml of dimethylformamide, and stirring continued for 2.5 hours. To the mixture was then added 6.77 g (0.044 mole) of 3-chlorophenyl ioscyanate, and stirring continued for a further 3.5 hours. Thereafter 200 ml of water was added to precipitate the desired N-(3-chlorophenyl)-N'-(1H-imidazol-2-yl)urea product, which is recovered by filtration and recrystallized from methanol to obtain as white solid pure N-(3-chlorophenyl)-N'-(1H-imidazol-2-yl)urea, m.p. 204°–214° C. (dec).

Anal: Calcd for $C_{10}H_9ClN_4O$: C, 50.75; H, 3.83; N, 23.63; Found: C, 50.62; H, 3.93; N, 23.63.

EXAMPLE IVA

N-(2,6-Dichlorophenyl)-N'-(1H-imidazol-2-yl)urea-4217

To a stirred solution of 4.78 g (0.04 mole) of 2-aminoimidazole hydrochloride in 50 ml of dimethylformamide was added dropwise 4.05 g (0.04 mole) of triethylamine and the resulting mixture stirred at ambient temperature for about one-half hour to obtain 2-aminoimidazole. To the reaction mixture was then added dropwise a solution of 7.52 g (0.04 mole) of 2,6-dichlorophenyl isocyanate in 12 ml of dimethylformamide, after which the resulting mixture was stirred at ambient temperature for about four hours to complete the formation of a N-(2,6-dichlorophenyl)-N'-(1$\underline{H}$-imidazol-2-yl)urea. Water (250 ml) was then added to precipitate the product, which is recovered by filtration and recrystallized from acetone/water (9:1) to obtain as a white solid pure N-(2,6-dichlorophenyl)-N'-(1$\underline{H}$-imidazol-2-yl)urea; m.p. (170° C.) 225°–227° C. (dec).

Anal: Calcd for $C_{10}H_8Cl_2N_4O$: C, 44.30; H, 2.97; N, 20.67; Found: C, 44.11; H, 3.01; N, 20.60; C, 44.17 H, 3.01 N, 20.66.

EXAMPLE IVB

N-(2,6-Dichlorophenyl)-N'-(1H-imidazol-2-yl)urea Hydrochloride-4217-11

A 34.6 g sample of the compound of Example IVA, as a suspension in one liter of methanol, was treated with etheral HCl (excess) until the solid dissolved. The solution was then treated with charcoal and filtered. The filtrate was concentrated in vacuo (water bath at 40°–45° C.) to give a white solid which was triturated with one liter of ether, filtered, and washed with ether. The crude salt was taken up in 600 ml of warm methanol, again treated with charcoal, filtered, and the filtrate concentrated to a volume of 350 ml in vacuo followed by dilution with ether to the cloud point (ca. 1200 ml of ether). Cooling (ca. 0°) gave pure product, which was then dried in vacuo (60° C.) to yield pure N-(2,6-Dichlorophenyl)-N'-(1$\underline{H}$-imidazol-2-yl)urea Hydrochloride; m.p. 234°–236° C. (dec), (variable with rate of heating. A slow heat rate gave m.p. 216°–235° C. dec).

Anal: Calcd for $C_{10}H_8Cl_2N_4O \cdot HCl$: C, 39.05; H, 2.95; Cl, 34.58; N, 18.22; Found: C, 39.04; H, 2.97; Cl, 34.53; N, 18.21.

EXAMPLE V

N-(2-Chloro-6-methylphenyl)-N'-(1H-imidazol-2-yl)urea-4257

Following the procedure of Example IV, 4.55 g (0.045 mole) of triethylamine was added to a stirred solution of 5.38 g (0.045 mole) of 2-aminoimidazole hydrochloride in 45 ml of dry dimethylformamide and the stirring continued for about ¾ hour at ambient temperature to obtain 2-aminoimidazole in the reaction mixture. To the reaction mixture was then added 7.54 g (0.045 mole) of 2-chloro-6-methylphenyl isocyanate and the mixture stirred for about four hours to obtain a N-(2-chloro-6-methylphenyl)-N'-(1$\underline{H}$-imidazol-2-yl)urea product. Water (450 ml) was added to precipitate the product which is then recovered by filtration and recrystallized from acetone/water to obtain pure N-(2-chloro-6-methylphenyl)-N'-(1$\underline{H}$-imidazol-2-yl)-urea; m.p. (194°) 226°–228° C. (dec).

Anal: Calcd for $C_{11}H_{11}ClN_4O$: C, 52.70; H, 4.42; N, 22.35; Found: C, 52.64; H, 4.43; N, 21.86; N, 21.93; N, 21.96.

EXAMPLE VI

In experiments carried out in a manner similar to those described in Examples I, III, and IV, the following compounds were prepared by the reaction of 2-amino-1-methylimidazole hydrochloride and triethylamine to form 2-amino-1-methylimidazole followed by the reaction of the latter with a molar equivalent of the appropriate aryl isocyanate:

4225-N-(2,6-diethylphenyl)-N'-(1$\underline{H}$-imidazol-2-yl)urea, m.p. 225°–250° C. (dec). (recrystallized from methanol/water).

Anal: Calcd for $C_{14}H_{18}N_4O$: C, 65.09; H, 7.02; N, 21.69; Found: C, 65.05; H, 7.16; N, 21.61; 65.01 H, 7.20 N, 21.66.

4227-N-(1$\underline{H}$-Imidazol-2-yl)-N'-[2-trifluoromethyl)-phenyl]urea, m.p. (180° C.) 208°–220° C. (dec). (recrystalized from absolute ethanol).

Anal: Calcd for $C_{11}H_9F_3N_4O$: C, 48.89; H. 3.36; N, 20.73; Found: C, 48.92; H, 3.37; N, 20.81.

4228-N-(1$\underline{H}$-Imidazol-2-yl)-N'-(3-methoxyphenyl)urea, m.p. 205°–230° C. (dec). (recrystallized from methanol).

Anal: Calcd for $C_{11}H_{12}N_4O_2$: C, 56.89; H, 5.21; N, 24.13; Found: C, 56.74; H, 5.21; N, 24.15;

4231-N-(1$\underline{H}$-Imidazol-2-yl)-N'-(2-methylphenyl)urea, m.p. (190° C.) 194°–230° C. (dec). (recrystallized from absolute ethanol and methanol).

Anal: Calcd for $C_{11}H_{12}N_4O$: C, 61.09; H, 5.59; N, 25.91; Found: C, 61.05; H, 5.61; N, 25.91.

4232-N-(1$\underline{H}$-Imidazol-2-yl)-N'-[3-(trifluoromethyl)-phenyl]-urea, m.p. 207°–235° C. (dec). (recrystallized from methanol).

Anal: Calcd for $C_{11}H_9F_3N_4O$: C, 48.89; H, 3.36; N, 20.73; Found: C, 48.80; H, 3.39; N, 20.76; C, 48.86 H, 3.38.

4238-N-(1$\underline{H}$-Imidazol-2-yl)-N'-(3-methylphenyl)-urea, m.p. 206°–235° C. (dec.). (recrystallized from methanol).

Anal: Calcd for $C_{11}H_{12}N_4O$: C, 61.09; H, 5.59; N, 25.91; Found: C, 61.35; H 5.18; N, 26.08; C, 61.34 H, 5.16.

4246-N-(2-Ethyl-6-methylphenyl)-N'-(1$\underline{H}$-imidazol-2-yl)-urea, m.p. (209°) 215°–245° C. (dec). (recrystallized from acetone/water).

Anal: Calcd for $C_{13}H_{16}N_4O$: C, 63.91; H, 6.60; N, 22.94; Found: C, 63.78; H, 6.66; N, 22.88.

4247-N-(2-Chlorophenyl)-N'-(1$\underline{H}$-imidazol-2-yl)urea, m.p. (194°) 198°–225° C. (dec). (recrystallized from methanol).

Anal: Calcd for $C_{10}H_9ClN_4O$: C, 50.75; H, 3.83; N, 23.67; Found: C, 50.71; H, 3.87; N, 23.69;

4307-N-(1$\underline{H}$-Imidazol-2-yl)-N'-(2,4,6-trimethylphenyl)-urea, m.p. 240° C. (dec). (recrystallized from DMF/ether).

Anal: Calcd for $C_{13}H_{16}N_4O$: C, 63.91; H, 6.60; N, 22.94; Found: C, 64.26; H, 6.66; N, 22.67.

4319-N-(2,6-Dibromophenyl)-N'-(1$\underline{H}$-imidazol-2)-yl)urea, m.p. (204°) 206°–220° C. (dec). (recrystallized from DMF/water and DMF/ether).

Anal: Calcd for $C_{10}H_8Br_2N_4O$: C, 33.36; H, 2.24; N, 15.56; Found: C, 33.42; H, 2.30; N, 15.41.

4320-N-[2,6-Bis(1-Methylethyl)phenyl]-N'-(1$\underline{H}$-imidazol-2-yl)urea, m.p. (242°) 245°–248° C. (dec.). (recrystallized from acetone/water and DMF/ether).

Anal: Calcd for $C_{16}H_{22}N_4O$: C, 67.10; H, 7.74; N, 19.57; Found: C, 66.95; H, 7.67; N, 19.61.

4326-N-(3,4-Dimethylphenyl)-N'-(1$\underline{H}$-imidazol-2-yl)urea, m.p. (207°) 213°–225° C. (dec). (recrystallized from DMF/water, THf, and DMF/ether).

Anal: Calcd for $C_{12}H_{14}N_4O$: C, 62.59; H, 6.13; N, 24.33; Found: C, 62.82; H, 6.19; N, 24.28.

4306-N-(4-Bromo-2,6-dimethylphenyl)-N'-(1$\underline{H}$-imidazol-2-yl)urea, m.p. 235° C. (dec). (recrystallized from acetone/water).

Anal: Calcd for $C_{12}H_{13}BrN_4O$: C, 46.62; H, 4.24; N, 18.12; Found: C, 46.60; H, 4.31; N, 17.88.

4382-N-(4-Chlorophenyl)-N'-(1H-Imidazol-2-yl)urea, m.p. (230°) 235°–238° C. (dec). (recrystallized from methanol and DMF/ether).

Anal: Calcd for C<sub>10</sub>H<sub>9</sub>ClN<sub>4</sub>O: C, 50.75; H, 3.83; N, 23.67; Found: C, 50.73; H, 3.89; N, 23.69.

4383-N-(1H-Imidazol-2-yl)-N'-(4-methylphenyl)urea, m.p. (219°) 225°–227° C. (dec). (recrystallized from DMF/ether).

Anal: Calcd for C<sub>11</sub>H<sub>12</sub>N<sub>4</sub>O: C, 61.09; H, 5.59; N, 25.91; Found: C, 61.08; H, 5.62; N, 25.93.

4422-N-(1H-Imidazol-2-yl)-N'-(2-methoxyphenyl)-urea, m.p. 202° 215°–232° C. (dec.). (recrystallized from acetone/water).

Anal: Calcd for C<sub>11</sub>H<sub>12</sub>N<sub>4</sub>O<sub>2</sub>: C, 56.89; H, 5.21; N, 24.13; Found: C, 56.87; H, 5.25; N, 23.80.

4423-N-(1H-Imidazol-2-yl)-N'-(4-methoxyphenyl)-urea, m.p. 204°–220° C. (dec.). (recrystallized from acetonitrile and acetone/water).

Anal: Calcd for C<sub>11</sub>H<sub>12</sub>N<sub>4</sub>O<sub>2</sub>: C, 56.89; H, 5.21; N, 24.13; Found: C, 56.87; H, 5.19; N, 24.05.

4483-N-(2,4-Dimethylphenyl)-N'-(1H-imidazol-2-yl) urea, m.p. 220° C. dec to new solid, m.p. 233°–236° C. (recrystallized from acetonitrile/DMF).

Anal: Calcd for C<sub>12</sub>H<sub>12</sub>N<sub>4</sub>O: C, 62.59; H, 6.13; N, 24.33; Found: C, 62.72; H, 6.20; N, 24.29.

4484-N-(2,5-dimethylphenyl)-N'-(1H-imidazol-2-yl)urea, m.p. 228° C. with decomposition to solid m.p. 242°–245° C. (dec). (recrystallized from DMF/methanol).

Anal: Calcd for C<sub>12</sub>H<sub>14</sub>N<sub>4</sub>O: C, 62.59; H, 6.13; N, 24.33; Found: C, 62.62; H, 6.19; N, 24.31.

4485-N-(1H-Imidazol-2-yl)-N'-(2,4,6-trichlorophenyl)-urea, m.p. 208°–210° C. (dec). (recrystallized from DMF/methanol/acetone-1:1:1).

Anal: Calcd for C<sub>10</sub>H<sub>7</sub>Cl<sub>3</sub>N<sub>4</sub>O: C, 39.31; H, 2.31; N, 18.34; Found: C, 39.74; H, 2.32; N, 18.06.

4481-99-N-(1H-Imidazol-2-yl)-N'-(2-isopropylphenyl)-urea 4/9 tert Butanol Solvate (by NMR), m.p. 180°–182° C. with decomposition to new solid m.p. 240°–245° C. (recrystallized from methanol by addition of t-butanol followed by acetone).

Anal: Calcd for C<sub>13</sub>H<sub>16</sub>N<sub>4</sub>O.4/9C<sub>4</sub>H<sub>10</sub>O: C,64.03; H, 7.42; N, 20.21; Found: C, 64.32; H, 7.36; N, 20.47.

4834-N-(2,6-Dimethoxyphenyl)-N'-(1H-imidazol-2-yl) urea, m.p. 219°–220° C. (recrystallized from DMSO/acetonitrile).

Anal: Calcd for C<sub>12</sub>H<sub>14</sub>N<sub>4</sub>O<sub>3</sub>: C, 54.96; H, 5.38; N, 21.36; Found: C, 54.92; H, 5.42; N, 21.36.

4836-N-(2,6-Difluorophenyl)-N'-(1H-imidazol-2-yl)urea, m.p. 195°–233° C. (dec). (recrystallized from DMF/acetonitrile).

Anal: Calcd for C<sub>10</sub>H<sub>8</sub>F<sub>2</sub>N<sub>4</sub>O: C, 50.43; H, 3.39; N, 23.52; Found: C, 50.49; H, 3.63; N, 23.54.

N-(2-Chloro-6-trifluoromethylphenyl)-N'-(1H-imidazol-2-yl)urea.

N-(1H-Imidazol-2-yl)-N'-(2-methyl-6-trifluoromethylphenyl)urea.

N-(1H-Imidazol-2-yl)-N'-(2-methoxy-6-triflouromethylphenyl) urea.

N-(1H-Imidazol-2-yl)-N'-(2,6-ditrifluoromethylphenyl)-urea.

The above Examples have been provided to illustrate the present invention without limiting the scope thereof, which scope is defined only in the appended claims.

What is claimed is:

1. A member selected from the group consisting of an imidazolylurea of formula

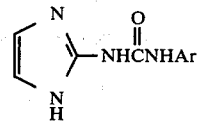

and the pharmaceutically-acceptable strong acid addition salts thereof wherein Ar is phenyl substituted with from one to two substituents each selected from the group consisting of halo, loweralkyl, loweralkoxy, and trifluoromethyl.

2. The compound of claim 1 wherein Ar is 2,6-disubstituted phenyl.

3. The compound of claim 2 wherein the substituents on Ar are each selected from the group consisting of chloro, bromo, methyl, and ethyl provided no more than one is ethyl.

4. A member selected from the group consisting of N-(2,6-Dichlorophenyl)-N'-(1H-imidazol-2-yl)urea and pharmaceutically-acceptable strong acid addition salts thereof.

5. A member selected from the group consisting of N-(2,6-Dimethylphenyl)-N'-(1H-imidazol-2-yl)urea and pharmaceutically-acceptable strong acid addition salts thereof.

6. A member selected from the group consisting of N-(2-Chloro-6-methylphenyl)-N'-(1H-imidazol-2-yl)urea and pharmaceutically-acceptable strong acid addition salts thereof.

7. A member selected from the group consisting of N-(2-Ethyl-6-methylphenyl)-N'-(1H-imidazol-2-yl) urea and pharmaceutically-acceptable strong acid addition salts thereof.

8. A member selected from the group consisting of N-(2,6-Dibromophenyl)-N'-(1H-imidazol-2-yl)urea and pharmaceutically-acceptable strong acid addition salts thereof.

9. A method of inhibiting gastric acid secretion in a gastric hyperacid subject which comprises systemically administering to said subject a therapeutically effective gastric acid secretion inhibiting amount of a compound of formula

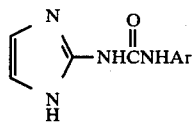

or a pharmaceutically-acceptable strong acid addition salt thereof, wherein Ar is phenyl substituted with from 1 to 2 substituents each selected from the group consisting of halo, loweralkyl, loweralkoxy, and trifluoromethyl; provided that Ar is other than 3-chlorophenyl.

10. A composition useful for treatment of gastric hyperacidity which comprises as active ingredient in admixture with a pharmaceutically-acceptable carrier from about 1 to about 500 mg of a compound of formula

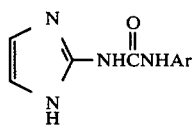

or a pharmaceutically-acceptable strong acid addition salt thereof, wherein Ar is phenyl substituted with from 1 to 2 substituents each selected from the group consisting of halo, loweralkyl, loweralkoxy, and trifluoromethyl provided that Ar is other than 3-chlorophenyl.

11. The composition of claim 10 wherein Ar is 2,6-disubstituted phenyl.

* * * * *